United States Patent
Mankovich et al.

(10) Patent No.: US 11,183,307 B2
(45) Date of Patent: Nov. 23, 2021

(54) CROWD-SOURCED TEXT ANNOTATION SYSTEM FOR USE BY INFORMATION EXTRACTION APPLICATIONS

(71) Applicant: KONINKLIJKE PHILIPS N.V., Eindhoven (NL)

(72) Inventors: Gabriel Ryan Mankovich, Boston, MA (US); Robbert Christiaan Van Ommering, Cambridge, MA (US); Lucas de Melo Oliveira, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 507 days.

(21) Appl. No.: 15/770,515

(22) PCT Filed: Oct. 26, 2016

(86) PCT No.: PCT/IB2016/056422
§ 371 (c)(1),
(2) Date: Apr. 24, 2018

(87) PCT Pub. No.: WO2017/077422
PCT Pub. Date: May 11, 2017

(65) Prior Publication Data
US 2018/0357210 A1  Dec. 13, 2018

Related U.S. Application Data

(60) Provisional application No. 62/251,130, filed on Nov. 5, 2015.

(51) Int. Cl.
*G16H 10/60* (2018.01)
*G06F 3/0482* (2013.01)
(Continued)

(52) U.S. Cl.
CPC ............ *G16H 70/00* (2018.01); *G06F 3/0482* (2013.01); *G06F 3/0484* (2013.01);
(Continued)

(58) Field of Classification Search
None
See application file for complete search history.

(56) References Cited

U.S. PATENT DOCUMENTS

| 2004/0073874 A1 | 4/2004 | Poibeau et al. |
| 2006/0026113 A1* | 2/2006 | Omoigui ............ G06F 17/30864 706/55 |

(Continued)

OTHER PUBLICATIONS

Zhai, H. et al., "Web 2.0-Based Crowdsourcing for High-Quality Gold Standard Development in Clinical Natural Language Processing", Journal of Medical Internet Research, vol. 15, No. 4, Apr. 2, 2013, p. e73.

(Continued)

*Primary Examiner* — Ariel Mercado

(57) ABSTRACT

The vocabulary of pertinent terms used to highlight/filter medical records in a text annotation system is continually updated based on user feedback. To maximize the effectiveness of this updating, feedback is extracted from all users of the system, thereby providing a 'group-sourced' vocabulary of pertinent terms. As each user modifies the provided vocabulary of pertinent terms to customize the text annotation system to conform to the user's preferences, the modifications are collected and communicated to the provider of the vocabulary of pertinent terms. The provider of the vocabulary of pertinent terms assimilates the modifications implemented by each user of the word annotation system to determine whether to modify the vocabulary of pertinent terms for subsequent users of the common vocabulary of pertinent terms.

16 Claims, 3 Drawing Sheets

(51) Int. Cl.
*G16H 70/00* (2018.01)
*G06F 40/169* (2020.01)
*G06F 3/0484* (2013.01)
*G16H 50/70* (2018.01)

(52) U.S. Cl.
CPC .......... *G06F 40/169* (2020.01); *G16H 10/60* (2018.01); *G16H 50/70* (2018.01)

(56) References Cited

U.S. PATENT DOCUMENTS

| | | | |
|---|---|---|---|
| 2009/0198514 A1* | 8/2009 | Rhodes | G06Q 50/22 705/3 |
| 2009/0276380 A1 | 11/2009 | Acero et al. | |
| 2011/0066425 A1 | 3/2011 | Hudgins et al. | |
| 2014/0223284 A1 | 8/2014 | Rankin et al. | |
| 2014/0317147 A1* | 10/2014 | Wu | G06F 17/30011 707/792 |
| 2015/0046190 A1 | 2/2015 | Strongwater | |
| 2015/0324454 A1* | 11/2015 | Roberts | G06F 17/30864 707/734 |

OTHER PUBLICATIONS

Hardiker, N. et al., "Collaborative development and maintenance of health terminologies", AMIA—Annual Sumposium proceedings/ AMIA Symposium, Nov. 16, 2013, pp. 572-577.

Culotta, A., "Corrective Feedback and Persistent Learning for Information Extraction", Elsevier Science. Aug. 31, 2006.

Anonymous: "Crowdsourcing—Wikipedia, the free encyclopedia", Feb. 11, 2015, pp. 1-21.

* cited by examiner

In 2007, the patient developed right-sided headaches, right-sided jaw pain, and right-sided toothaches. Initial workup of the symptoms resulted in a CT of the sinuses, which was originally reported as normal.

FIG. 1A

In 2007, the patient developed RIGHT-SIDED HEADACHES, RIGHT-SIDED PAIN, and RIGHT-SIDED TOOTHACHES. Initial workup of the symptoms resulted in a CT OF THE SINUSES, which was originally reported as NORMAL.

FIG. 1B

RIGHT-SIDED HEADACHES
RIGHT-SIDED PAIN
RIGHT-SIDED TOOTHACHES
CT OF THE SINUSES
NORMAL.

FIG. 1C

CROWD-SOURCED TEXT ANNOTATION SYSTEM FOR USE BY INFORMATION EXTRACTION APPLICATIONS

This application is the U.S. National Phase application under 35 U.S.C. § 371 of International Application No. PCT/IB2016/056422, filed on Oct. 26, 2016, which claims the benefit of U.S. Patent Application No. 62/251,130, filed on Nov. 5, 2015. These applications are hereby incorporated by reference herein.

FIELD OF THE INVENTION

This invention relates to the field of medical information systems, and in particular to a system and method that uses user feedback to identify pertinent words or phrases for efficient and effective data extraction from text documents

BACKGROUND OF THE INVENTION

Effective medical diagnosis and treatment requires an assessment of a patient's current medical condition as well as the patient's medical history. If the patient has been with the same primary practitioner for an extended period, the primary practitioner is likely to be aware of the patient's medical history; but as situations change, patients are likely to need to visit either a new primary practitioner or, more commonly, a practitioner from another discipline. These other practitioners do not have the benefit of the original practitioner's experience. In like manner, particularly with regard to medical specialties, the practitioner may see the patient infrequently, and cannot be expected to remember the medical history of each patient.

In such situations, the practitioner must spend time reviewing the patient's medical history to assimilate the patient's current condition before developing a diagnosis and prognosis. The task of reviewing a patient's medical history is facilitated by the availability of electronic medical records, and computer applications that facilitate an efficient review of these records. For example, a cardiologist may restrict the review of a patient's records to material that is identified as being related to the cardiac system. Such systems, however, typically require that the medical record information be organized in a particular manner, including, for example, specific HTML, fields that can be used to identify which records may be pertinent to the practitioner's field.

Some of the patient's records may, however, be in free-form text, and may include information that the practitioner may find to be pertinent. Having to read such text records, however, consumes the practitioner's time, often without the disclosure of pertinent information.

Tools have been developed to facilitate an efficient review of free-form text records, as illustrated in FIGS. 1A-1C. FIG. 1A illustrates a display of the free-form text record. FIG. 1B illustrates a display of this text provided by a text annotation system that highlights the words and phrases that are pertinent to the diagnosis of the patient (hereinafter 'pertinent terms'), so that the practitioner's attention is directed to these pertinent terms. FIG. 1C illustrates a display of only the pertinent terms in the free-form text to potentially further direct the practitioner's attention to these pertinent aspects in the patient's record.

In some embodiments, the display provides only the pertinent terms as in FIG. 1C, but when the practitioner "mouses over" the displayed text (i.e. moves the mouse pointer to within the display area of the text), the display changes to a display of the entire free-form text, such as illustrated in either FIG. 1A or 1B. Other methods of 'selecting' the displayed text for displaying some or all of the free-form text of the patient record would be evident to one of skill in the art.

A key to the effectiveness of conventional text annotation systems is the proper identification of such "pertinent terms", and the options provided to the practitioner for defining such pertinent terms. In some embodiments, the pertinent terms may be derived from a general medical ontology, or a specialized ontology for a particular medical specialty. These pertinent terms may be defined by the provider of the text annotation system, or developed by the provider based on interactions with a medical facility or organization that is implementing such a system. In some embodiments, the individual user of the system may amend or supplement the vocabulary of pertinent terms.

Even with an extensive vocabulary of pertinent terms, however, because a free-form text record is not necessarily constrained to conform to such a defined vocabulary, and because the vernacular changes to the vocabulary may outpace the changes to the defined vocabulary, and because the creators of the vocabulary may not be actively engaged practitioners, the identification of pertinent terms in a patient's record may omit some newly identified pertinent terms, or may be so inclusive as to minimize the effectiveness of the text annotation system by highlighting minimally pertinent, or even irrelevant terms, thereby obscuring the actually pertinent terms.

SUMMARY OF THE INVENTION

It would be advantageous to provide a text annotation system that accurately and reliably highlights pertinent terms in a patient's record. It would also be advantageous to provide a text annotation system that is able to keep pace with changing medical diagnostic technology and vocabulary.

To better address one or more of these concerns, in an embodiment of this invention, the vocabulary of pertinent terms used to highlight/filter medical records in a text annotation system is continually updated based on user feedback. To maximize the effectiveness of this updating, feedback is extracted from all users of the system, thereby providing a 'group-sourced' vocabulary of pertinent terms. As each user modifies the provided vocabulary of pertinent terms to customize the text annotation system to conform to the user's preferences, the modifications are collected and communicated to the provider of the vocabulary of pertinent terms. The provider of the vocabulary of pertinent terms assimilates the modifications implemented by each user of the word annotation system to determine whether to modify the vocabulary of pertinent terms for subsequent users of the common vocabulary of pertinent terms.

In one exemplary embodiment, a text annotation system is configured to receive a vocabulary of pertinent terms from a provider that provides the vocabulary to a plurality of practitioners, then processes a patient record to identify pertinent terms in the patient record based on the vocabulary of pertinent terms. The identified pertinent terms in the patient record are displayed in a distinctive manner to the practitioner, and the practitioner's modifications to the vocabulary of pertinent terms are recorded. These modifications of the vocabulary are communicated to the provider of the vocabulary, along with modifications from other users of this vocabulary. Thereafter, the text annotation system receives an updated vocabulary of pertinent terms from the provider based on these modification of the vocabulary.

A crowd sourced knowledge module provides a common vocabulary of pertinent terms to a plurality of text annotation systems, then receives modifications to the vocabulary of pertinent terms from the text annotation systems. The module assimilates the modifications to the vocabulary to determine whether an update to the vocabulary of pertinent terms is warranted, and if so, updates the vocabulary of pertinent terms and subsequently provides the updated vocabulary of pertinent terms to the text annotation systems.

A network of text annotation systems is provided that comprises: a database that stores a vocabulary of pertinent terms that may be used in a medical record; a plurality of text annotation systems that each highlight pertinent terms in a patient's medical record based on the vocabulary of pertinent terms, and receives a user's proposed modifications to the vocabulary of pertinent terms; and a crowd-sourced knowledge module that provides the vocabulary of pertinent terms at the database to the plurality of text annotation systems, receives the proposed modifications to the vocabulary of pertinent terms from the plurality of text annotation systems, assimilates the proposed modifications to the vocabulary to determine whether an update to the vocabulary of pertinent terms is warranted, and updates the vocabulary of pertinent terms when the update is determined to be warranted.

BRIEF DESCRIPTION OF THE DRAWINGS

The invention is explained in further detail, and by way of example, with reference to the accompanying drawings wherein:

FIG. 1A illustrates an example free-form text medical record.

FIG. 1B illustrates an annotation of the free-form text of FIG. 1A to highlight pertinent terms in the free-form text medical record.

FIG. 1C illustrates an alternative annotation of the free-form text of FIG. 1A to display on the pertinent terms in the free-form text medical record.

Throughout the drawings, the same reference numerals indicate similar or corresponding features or functions. The drawings are included for illustrative purposes and are not intended to limit the scope of the invention.

DETAILED DESCRIPTION

Figure 2:
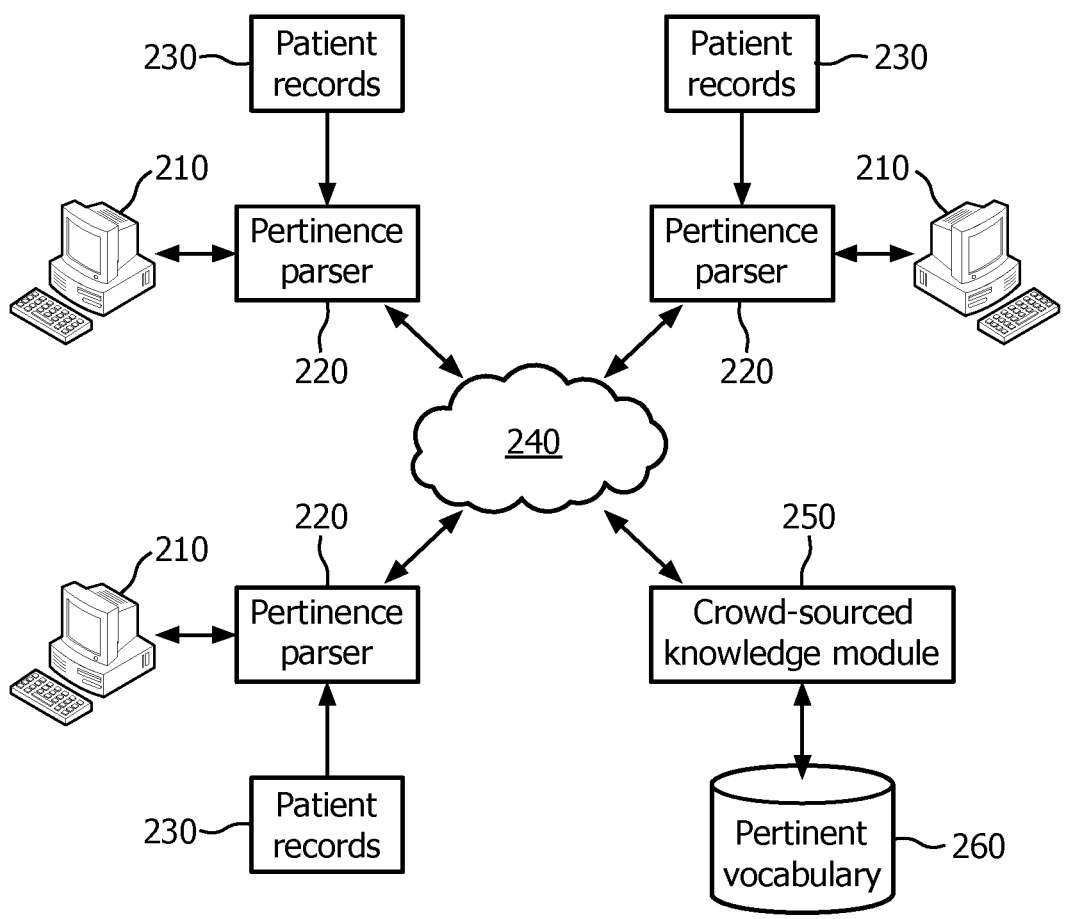
FIG. 2 illustrates an example network of text annotation systems that share a common vocabulary of pertinent terms that is continually updated based on feedback provided by the users of this network of text annotation systems in accordance with aspects of this disclosure.

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

This disclosure recognizes that reliance on a sole source of 'knowledge' has substantial limitations. In the case of defining pertinent terms in a patient record, the definition of which terms are pertinent or non-pertinent conventionally relies on the 'knowledge' of the person or organization that creates the vocabulary of pertinent terms. Although some systems may enable each user to customize the vocabulary in accordance with that user's preferences, such customizations are limited to that particular user's expertise in distinguishing between pertinent and non-pertinent terms, as contrast to the provided vocabulary of pertinent terms.

For example, a novice practitioner may not recognize why a particular term may be pertinent and may assume that the vocabulary is out-of-date and modify his/her personal vocabulary to remove that term from the vocabulary of pertinent terms. In like manner, another practitioner may have had some experience that indicates to this practitioner that the vocabulary should be expanded to include a term that was omitted from the vocabulary of pertinent terms. In each case, the practitioner is confident that, based on the practitioner's knowledge base, the removal from or addition to the vocabulary is warranted; but, from an objective viewpoint, whether or not these particular modifications are 'valid' is unknown.

Accordingly, if a system enables a user to modify the vocabulary of pertinent terms, the user's modified vocabulary may not be consistent with generally accepted definitions of pertinent and non-pertinent information. On the other hand, a system that is constrained to the vocabulary of pertinent terms that is defined by a provider of the vocabulary runs the risk of becoming outdated unless the provider of the vocabulary is vigilant in keeping the vocabulary up-to-date as the knowledge in the medical community grows or changes.

The inventor has recognized that a networking of practitioners having access to a common vocabulary of pertinent terms enables the following features:

providing user flexibility in customizing the vocabulary;
enabling a validation of such customization; and,
providing a continuingly validated vocabulary of pertinent terms to the plurality of users of this vocabulary in their text annotations systems.

FIG. 2 illustrates such a network of practitioners having access to a common vocabulary of pertinent terms. Each practitioner is provided a text annotation system 210 that includes a parser 220 that identifies pertinent terms in one or more patient's records 230. In an example embodiment, the patient's record(s) may include free-form text such as illustrated in FIG. 1A.

The parser 220 identifies each occurrence of a pertinent term in the patient's record and displays the pertinent terms in a distinctive manner, as illustrated in either of FIGS. 1B and 1C. If the initial display is as illustrated in FIG. 1C, wherein only the pertinent terms are displayed, the practitioner may 'select' the display to enable a display of the full text, as illustrated in either of FIG. 1A or 1B.

A vocabulary 260 of the pertinent terms may be commonly provided to all of the pertinence parsers 220 via the network 240. In accordance with an aspect of this disclosure, a crowd sourced knowledge module 250 is configured to update this vocabulary 260 based on feedback from the users of the text annotation systems 210.

In an example embodiment, each user of the text annotation system 210 is provided the option of locally modifying the vocabulary of pertinent terms, to identify, for example, terms in the art that have newly been found to be pertinent, or to remove terms that are no longer deemed to be pertinent, and so on. When such modifications are made, the modifications are communicated to the crowd sourced knowledge module 250. This communication may occur in real time, as the modifications are made, or at periodic intervals, such as daily or at the end of each work-shift at the medical facility that provides the text annotation system 210.

The crowd sourced knowledge module 250 may be configured to assimilate all of the modifications received as they are received, or periodically, and determine what modifications, if any, should be made to the commonly provided vocabulary 260 based on the received modifications from the users of the text annotation systems 210. In some embodiments, the vocabulary 260 is continuously updated; in other embodiments, the vocabulary 260 is updated based on the modifications received over a defined time period, such as every few hours, or daily.

After updating the vocabulary 260, the module 250 may 'broadcast' the updated vocabulary 260 to each of the text annotation systems 210, or the updated vocabulary 260 may be provided in response to specific requests for the vocabulary 260 from each text annotation system 210. The broadcast may be scheduled to occur periodically, or whenever a change is made to the vocabulary 260.

Any number of techniques may be used to assimilate the modifications received from the text annotation systems 210, typically based on a tradeoff between the risk of omitting a pertinent term from the vocabulary 260 and the risk of obscuring the display of pertinent terms in a report with non-pertinent terms.

In some embodiments, a simple voting scheme may be used, wherein if more users choose to add a term to the pertinent vocabulary 260 than to delete the term from the pertinent vocabulary 260, the term is added to the vocabulary 260; otherwise the term is deleted from the vocabulary 260. If, on the other hand, the risk of omitting a relevant term from the vocabulary 260 is considered to be more significant that the risk of potentially including non pertinent terms in the vocabulary 260 (hereinafter 'cluttering'), the term may be added to the vocabulary 260 whenever a user modifies the local vocabulary to include the term, but only deletes a term from the vocabulary 260 when the number of modifications for removal of the term is significantly greater than the number of modifications for adding the term to the vocabulary 260.

In some embodiments, a weighted accumulation may be maintained wherein, for example, a modification to add a term to the vocabulary 260 may be valued as a large positive number, and a modification to remove the term from the vocabulary may be valued as a small negative number, and the term remains in the vocabulary 260 whenever the accumulation is greater than zero. If, on the other hand, the risk of cluttering is considered to outweigh the risk of omission, the modifications to add a term may be given a small positive value and the modifications to delete a term may be given a large negative value.

In some embodiments, recent modifications may be considered to be more significant than older modifications, and a rolling average may be maintained wherein more recent modifications are weighted more than older modification.

One of skill in the art will recognize that this crowd sourced feedback scheme effectively provides a 'sampling' system for determining which terms are likely to be considered pertinent by the general population of users of the text annotation systems 210. Accordingly, statistical techniques may also be used to assimilate the modification 'samples' so as to only provide changes to the vocabulary 260 when it can be shown that the modifications are 'statistically significant'.

The assimilation may also consider the effect of "non-modifications". That is, for example, if a user does not modify the vocabulary while using the vocabulary 260 to review a patient's records, it may be assumed that the user agrees with the content of the vocabulary 260 with respect to the identified pertinent terms in the review of the patient's records, and this 'passive agreement' should affect any decision to delete these terms from the vocabulary 260. In some embodiments, the feedback provided from the text annotation system 210 may include a list of the pertinent terms that were displayed to the user (and not marked for removal), or, more selectively, a list of the pertinent terms that were displayed in a window that the user selected to display the full text of the record. These terms may receive, for example, a small positive value in the aforementioned accumulation, thereby reducing the likelihood of removing these 'passively accepted' terms until a substantial number of users indicate a preference for their removal. Such a passive reinforcement of existing terms in the vocabulary 260 may obviate the need to use the aforementioned weighted values to offset the effect of modifications that would remove terms from the vocabulary 260.

The assimilation may also be configured to set a 'threshold' value for initially adding a term to the vocabulary 260, to avoid unnecessary 'chatter' when a single user modifies the vocabulary to include a new term. Because this would be the only 'vote' regarding the term, in a conventional voting scheme this vote would likely result in a change to the vocabulary 260 to include this term. However, this new term may likely be considered non-pertinent by many of the other users, resulting in numerous subsequent modifications to remove the term from the vocabulary. To avoid such a situation, the assimilation may be configured to only add a new term to the vocabulary 260 when a given number of users modify the vocabulary to include this term. This minimum-number-of-users threshold scheme may also be effective in minimizing the risk of having a malicious user adding a "commonly used" term that will obviously lead to cluttering of the displays of all users, at least until the feedback is received to remove this term.

One of skill in the art will recognize that this continuous feedback of user modifications to the crowd sourced knowledge module and subsequent updating of the common vocabulary 260 of pertinent changes may produce transient effects as changes are made to the vocabulary 260, then countermanded by reactionary feedback, but the eventual 'stabilized' terms in the common vocabulary 260 are likely to be agreeable to the majority of users of the text annotation systems 210 that use this vocabulary 260.

Figure 3:
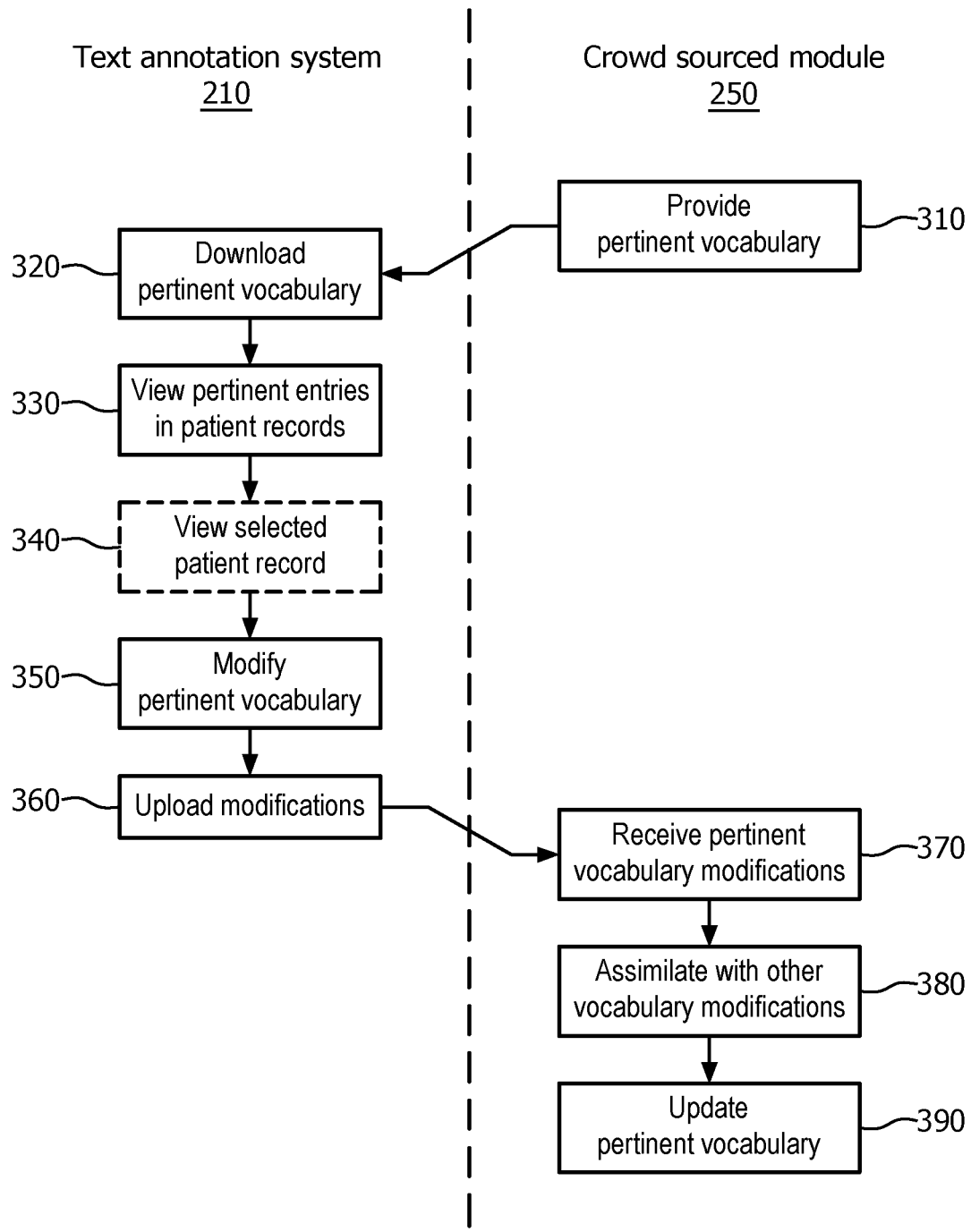
FIG. 3 illustrates a flow diagram of an example use of a text annotation system that uses a vocabulary of pertinent terms that is commonly used by a plurality of users, wherein the vocabulary of pertinent terms is continually updated based on feedback provided by the plurality of users in accordance with aspects of this disclosure.

FIG. 3 illustrates a flow diagram of an example use of a text annotation system in accordance with aspects of this disclosure. The left column indicates actions taken at the text annotation system, such as the system 210 of FIG. 2, and the right column indicates actions taken by the crowd sourced knowledge module 250 of FIG. 2.

At 310, the module 250 provides the vocabulary of pertinent terms to the text annotation system 210. This may be performed as a broadcast to all of the text annotation systems 210 in the network, or it may be performed in response to a request for the vocabulary from the text annotation system 210.

At 320, the vocabulary of pertinent terms is downloaded at the text annotation system 210, and used, at 330, to parse a patient's record(s) and display any pertinent terms in the patient's record in a distinctive manner, such as highlighted within a display of a free-text record (e.g. FIG. 1B), or displayed without the non-pertinent terms in the patient's record (e.g. FIG. 1C).

Optionally, at 340, the user may select the displayed information by, for example, placing a mouse pointer over the displayed information, or by 'clicking' or 'double-clicking' on the displayed information.

If the user desires to modify the vocabulary of pertinent terms, to add or delete a term, for example, the user may effect such a modification at 350. In an example embodiment, the user may 'right click' on a term to change its status. If the term is currently a pertinent term in the vocabulary, its status is changed to non-pertinent and removed from the local copy of the vocabulary at the text annotation system; if the term is currently a non-pertinent term, its status is changed to pertinent and added to the local copy of the vocabulary. The text annotation system then updates the display of pertinent terms in the patient's record(s) based on this change to the local vocabulary.

At 360, any modifications to the local vocabulary are communicated from the text annotation system 210 to the crowd sourced knowledge module 250. As noted above, the modifications may be communicated as they are made, or at periodic or aperiodic intervals.

At 370, the modifications are received at the module 250, along with any modifications from other text annotation systems 210. These modifications are assimilated by the module 250, at 380, to determine whether a change to the vocabulary of pertinent terms is warranted. As detailed above, a weighted or unweighted voting scheme, preferably with thresholding, may be used to determine the changes that are likely to be agreeable to the population of users of the text annotation systems 210.

At 390, the determined changes to the vocabulary of pertinent terms are implemented, so that the next time the vocabulary is sent from the module 250, at 310, it includes these changes.

As noted above, this disclosure provides an automated method of keeping a vocabulary of pertinent terms up-to-date, while at the same time, providing affirmation that each stabilized revision of the vocabulary is likely to be agreeable to a substantial majority of the users of the text annotation systems that use this vocabulary.

While the invention has been illustrated and described in detail in the drawings and foregoing description, such illustration and description are to be considered illustrative or exemplary and not restrictive; the invention is not limited to the disclosed embodiments.

For example, in an alternative embodiment, each user of the text annotation system 210 may maintain a 'private' supplemental vocabulary that augments the vocabulary 260 that is received from the crowd sourced knowledge module 250. The supplemental vocabulary may be configured to identify terms in the vocabulary 260 that are to be considered non-pertinent, and to identify additional terms, which may or may not be in the vocabulary 260, that are always to be considered as pertinent.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A non-transitory computer readable medium that includes a program that, when executed by a processing system, causes the processing system to:
receive a vocabulary of pertinent terms from a provider that provides the vocabulary to a plurality of practitioners;
receive a request from a practitioner for a patient record;
process the patient record to identify pertinent terms in the patient record based on the vocabulary of pertinent terms;
display the identified pertinent terms in the patient record in a distinctive manner to the practitioner;
receive, from the practitioner, a selection of a displayed pertinent term, and an identification of a proposed modification to remove the selected pertinent term from the vocabulary of pertinent terms;
communicate the proposed modification of the vocabulary to the provider of the vocabulary; and
subsequently receiving an updated vocabulary of pertinent terms from the provider of the vocabulary;
wherein the updated vocabulary is based on the proposed modification of the vocabulary by the practitioner and also based on one or more proposed modifications from the plurality of practitioners to add a new term to the vocabulary of pertinent terms, and one or more proposed modifications to remove an existing term from the vocabulary of pertinent terms.

2. The medium of claim 1, wherein the program causes the processor to:
display one or more non-pertinent terms in the patient's record,
receive, from the practitioner, a selection of a displayed non-pertinent term, and an other proposed modification that the selected non-pertinent term in the patient's record should be added to in the vocabulary of pertinent terms, and communicate the other proposed modification to the provider of the vocabulary.

3. The medium of claim 1, wherein the program causes the processor to display the identified pertinent terms in a distinctive manner by displaying only the pertinent terms.

4. The medium of claim 3, wherein the program causes the processor to subsequently display an entire content of at least a portion of the patient record when the practitioner indicates selection of a display area containing the pertinent terms.

5. The medium of claim 1, wherein the program causes the processor to display the identified pertinent terms in a distinctive manner by displaying the pertinent terms using a different display format than other terms in the patient record.

6. The medium of claim 1, wherein the updated vocabulary of pertinent terms is based on a count of the modifications to add the selected pertinent term to the vocabulary of pertinent terms, and the modifications to remove the selected pertinent term from the vocabulary.

7. The medium of claim 6, wherein the count of modifications is a weighted accumulation, wherein a first weight is applied to each modification to add the selected pertinent term to the vocabulary and a second weight is applied to each modification to remove the selected pertinent term from the vocabulary.

8. A non-transitory computer readable medium that includes a program that, when executed by a processing system, causes the processing system to:
provide a vocabulary of pertinent terms to a plurality of text annotation systems;
receive proposed modifications to the vocabulary of pertinent terms from two or more of the plurality of text annotation systems, wherein the proposed modifications include modifications that add a term to the vocabulary and modifications that remove a term from the vocabulary;
assimilate the proposed modifications to the vocabulary to determine whether an update to the vocabulary of pertinent terms is warranted;
updating the vocabulary of pertinent terms if and only if the update is determined to be warranted; and
providing the updated vocabulary of pertinent terms to one or more of the pluralities of text annotation systems.

9. The medium of claim 8, wherein the program causes the processor to assimilate the modifications by maintaining a count of the modifications that add the term to the vocabulary of pertinent terms and the modifications that remove the term from the vocabulary.

10. The medium of claim 9, wherein the count of modifications is a weighted accumulation, wherein a first weight is applied to each modification that adds the term to the vocabulary and a second weight is applied to each modification that removes the term from the vocabulary.

11. The medium of claim 9, wherein a non-zero threshold is applied to the count of modifications to determine whether an update to the vocabulary is warranted.

12. A network of computer-based systems comprising:
a computer-readable database that stores a vocabulary of pertinent terms that may be used in a medical record;
a plurality of computer-based text annotation systems that each:
highlight pertinent terms in a display of a patient's medical record based on the vocabulary of pertinent terms; and
receive proposed modifications to the vocabulary of pertinent terms by a user of the text annotation system;
a computer-based crowd-sourced knowledge module that:
provides the vocabulary of pertinent terms at the database to the plurality of text annotation systems;
receives the proposed modifications to the vocabulary of pertinent terms from the plurality of text annotation systems, wherein the proposed modifications include modifications that add a term to the vocabulary and modifications that remove a term from the vocabulary;
assimilates the proposed modifications to the vocabulary to determine whether an update to the vocabulary of pertinent terms is warranted;
updates the vocabulary of pertinent terms if and only if the update is determined to be warranted; and
provides the updated vocabulary of pertinent terms to one or more of the pluralities of text annotation systems.

13. The network of claim 12, wherein at least one of the text annotation systems displays one or more non-pertinent terms in the patient's record, and enables a user to select a non-pertinent term so as to indicate that the proposed modification is to add the select non-pertinent term to the vocabulary of pertinent terms.

14. The network of claim 12, wherein at least one of the text annotation systems enables a user to select a displayed pertinent term so as to indicate that the proposed modification is to remove the select pertinent term from the vocabulary of pertinent terms.

15. The network of claim 14, wherein the crowd-sourced knowledge module assimilates the proposed modifications by maintaining a count of the modifications that add a term to the vocabulary of pertinent terms and the modifications that remove the term from the vocabulary.

16. The network of claim 15, wherein the count of modifications is a weighted accumulation, wherein a first weight is applied to each proposed modification that adds the term to the vocabulary and a second weight is applied to each proposed modification that removes the term from the vocabulary.

* * * * *